United States Patent
Jenkins, Jr.

(10) Patent No.: US 6,981,504 B2
(45) Date of Patent: Jan. 3, 2006

(54) CORE STIFFENED EARPLUG

(75) Inventor: John Allen Jenkins, Jr., San Marcos, CA (US)

(73) Assignee: Bacou-Dalloz USA Safety, Inc., San Diego, CA (US)

(*) Notice: Subject to any disclaimer, the term of this patent is extended or adjusted under 35 U.S.C. 154(b) by 0 days.

(21) Appl. No.: 10/869,331

(22) Filed: Jun. 16, 2004

(65) Prior Publication Data

US 2005/0039761 A1 Feb. 24, 2005

Related U.S. Application Data

(60) Provisional application No. 60/497,377, filed on Aug. 21, 2003.

(51) Int. Cl.
*A61F 11/00* (2006.01)

(52) U.S. Cl. .................. 128/864; 128/864; 128/865; 128/867; 181/130; 181/135; 381/380

(58) Field of Classification Search .............. 128/864, 128/865, 866, 867, 868; 181/128, 129, 130, 181/134, 135

See application file for complete search history.

(56) References Cited

U.S. PATENT DOCUMENTS

| | | | | |
|---|---|---|---|---|
| 3,736,929 A | * | 6/1973 | Mills | ........................... 128/864 |
| 4,434,794 A | | 3/1984 | Leight | |
| 5,573,015 A | | 11/1996 | Williams | |
| 5,799,658 A | * | 9/1998 | Falco | ........................... 128/864 |
| 6,659,103 B2 | | 12/2003 | Tiemens | |

* cited by examiner

*Primary Examiner*—Henry Bennett
*Assistant Examiner*—Camtu Nguyen
(74) *Attorney, Agent, or Firm*—Leon D. Rosen

(57) ABSTRACT

An earplug of the type that includes a soft foam body (14) and a more rigid core (16) that stiffens the body during its insertion into the ear canal, is mass produced so the front end (30) of the stiff core cannot rub along the surface of the ear canal during insertion. The core is elongated and bonded to the body, and the core has a front end (30) that is recessed from the front end (36) of the body, so the soft foam material of the body prevents the front end of the core from contacting the ear canal. The earplug can be mass produced by extruding the soft foam through an extrusion head (42), around the cores, with a long core device having been cut into the cores and with the extrusion (52) cut at locations to leave foam material forward of each core front end.

8 Claims, 2 Drawing Sheets

CORE STIFFENED EARPLUG

This application claims benefit of 60/497,377 Aug. 21, 2003.

BACKGROUND OF THE INVENTION

One type of earplug that is used to block intense noise from entering workers' ear canals, includes a body of soft resilient foam material that is of greater diameter than the ear canal and that is inserted into the ear canal. Such insertion can be attempted by the worker placing the front end of the soft foam earplug body against the entrance to his/her ear canal, and then pressing forwardly against the rear end of the foam body. In practice, it is found to be almost impossible to insert the earplug by pressing against its rear end. Since the body front portion has a greater diameter than the ear canal, the earplug meets resistance, and since the body is soft it tends to buckle. One solution is to form the body of slow recovery foam material that can be rolled in the fingers to a small diameter, inserted into the ear canal, and held there until it expands. However, the earplug tends to become dirty if the worker's fingers are dirty.

It is found that insertion of a very soft body such as one formed of soft foam, can be facilitated by the use of a core that is much stiffer than the body and that has a front end lying deep in the body. U.S. Pat. No. 4,434,794 shows a core or stiffener that can be slid into a shell-shaped body to help its insertion. U.S. Pat. Nos. 5,573,015 and 6,659,103 show a stiffener lying within and bonded to a foam body and manufactured by extrusion. One problem encountered in the use of a stiffener or core such as the type shown in U.S. Pat. No. 5,573,015, is that there is a possibility that the front end of the core will rub against the ear canal during earplug insertion, especially if the person's ear canal is highly curved. Even if such rubbing is unlikely, people who are required to wear the earplug may be concerned about the possibility of such rubbing, especially if they press a finger against the front end of the earplug and notice the stiff core at the front end. An earplug with a stiffener, that avoided the possibility of the stiffener front end scraping against the wearer's ear during insertion, and that could be mass produced at low cost, would be of value.

SUMMARY OF THE INVENTION

In accordance with one embodiment of the present invention, an earplug and production method are provided that result in an earplug with a body of soft elastomeric material such as a soft foam, that can be readily inserted into the ear canal without soiling the earplug, and without danger of harm to the ear canal. The earplug includes a stiffener, or core that is much stiffer than the foam earplug body, and which extends along the axis of the body and which is bonded to the body. The core is elongated, with front and rear ends lying close, respectively, to the front and rear ends of the soft foam body. However, the front end of the core lies rearward of the front end of the body. This results in the front of the soft foam body preventing the front end of the core from touching the ear canal of even a highly curved ear canal.

The earplug can be formed by extrusion of a foamable material rearwardly though an extrusion head, while a stiffener core is also moved rearwardly through the extrusion head. The cores can be precut from a long core device, and moved though the extrusion head with a gap between subsequent cores. The extrusion is cut at locations slightly forward of the front end of each core, so extruded foam material lies in front of the front end of each core. In another process, a long continuous core device is moved though the extrusion head, within the foam that is being extruded, and the extrusion is periodically cut immediately after emerging from the head and while the foamable material is still expanding. This results in the foam expanding forward of the rod which is not foaming or otherwise expanding.

The novel features of the invention are set forth with particularity in the appended claims. The invention will be best understood from the following description when read in conjunction with the accompanying drawings.

DESCRIPTION OF THE PREFERRED EMBODIMENTS

Figure 1:
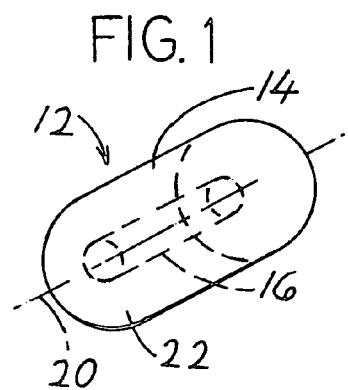
FIG. 1 is an isometric view of an earplug of one embodiment of the invention.
Figure 2:
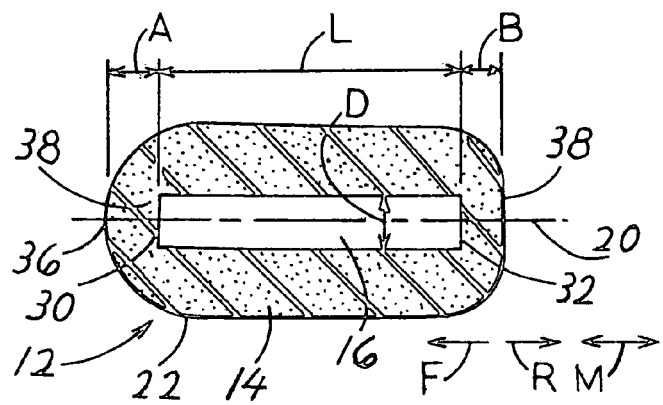
FIG. 2 is a sectional view of the earplug of FIG. 1.

FIGS. 1 and 2 illustrate an earplug 12 of one embodiment of the invention, which includes an earplug body 14 of soft resilient foam, and a stiffener or core 16 that extends along the axis 20 of the body. The body 14 has a front portion 22 of a diameter such as 0.4 inch to enter a person's ear canal, which has a diameter such as 0.3 inch, and form a sound-tight seal against it. The body is formed of a soft elastomeric material, having a durometer of 1 to 10, shore A. An elastomeric material may be defined as one with a Young's modulus of elasticity of no more than 50,000 psi. As mentioned above, such a soft body alone will collapse when the body front portion is pushed against the entrance of an ear canal. The core 16 is of material much stiffer than that of the body, such as a soft rubber which has a durometer of at least 30 shore A. However, the core is soft enough so it will bend when the earplug enters a curved ear canal.

The core is preferably made of a nonfoam elastomer such as rubber, and may be a solid post or a rubber tube that is hollow and filled with foam. The stiffness of the core material is more than twice that of the body, and its stiffness (per unit cross-sectional area) against compression between its opposite ends 30, 32, is more than twice the stiffness of the body when the body alone is compressed between its opposite ends 34, 36. The core 16 is elongated in the longitudinal direction M, with a length L more than twice its diameter D. The core diameter is small to allow the soft foam material of the body to be easily compressed in diameter. The core lies on the axis 20 of the body, which also extends in the longitudinal direction.

Figure 10:
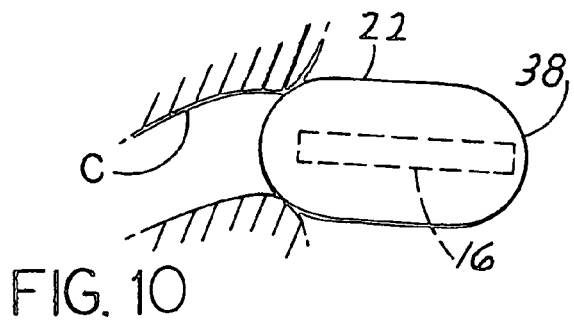
FIG. 10 is a sectional view of a person's ear canal, and shows an earplug as it begins the insertion process.

The front end 30 of the core 16 lies a distance A rearward R of the front end 36 of the body 14. In FIG. 2, the core front end is not exposed because a body front part 38 lies directly in front of the entire area of the core front end 30. The core is bonded to the body, which can be done by foaming a foamable body material around the core during an extrusion or other molding process. The earplug 12 can be inserted into a person's ear by the person placing the front portion 22 of the body against the entrance to the ear canal C, as shown in FIG. 10. The person presses against the earplug rear end 38. The pressing force is transmitted by the core 16 (which is bonded to the body) to the front portion 22 of the body to press it into the ear canal. Applicant prefers that the rear end 32 (FIG. 2) of the core lie a distance B of more than a millimeter forward of the body rear end, so the entire earplug has a soft touch to minimize apprehension of the person who will wear it. The core front end 30 is recessed a distance A of a plurality of millimeters from the body front end. The earplug 12 can be inserted into a person's ear by the person placing the front portion 22 of the body against the entrance to the ear canal, as shown in FIG. 10. The person presses against the earplug rear end 38. The pressing force is transmitted by the core 16 (which is bonded to the body) to the front portion 22 of the body to press it into the ear canal. Applicant prefers that the rear end 32 (FIG. 2) of the core lie a distance B of more than a millimeter forward of the body rear end, so the entire earplug has a soft touch to minimize apprehension of the person who will wear it. The core front end 30 is recessed a distance A of a plurality of millimeters from the body front end.

Figure 3:
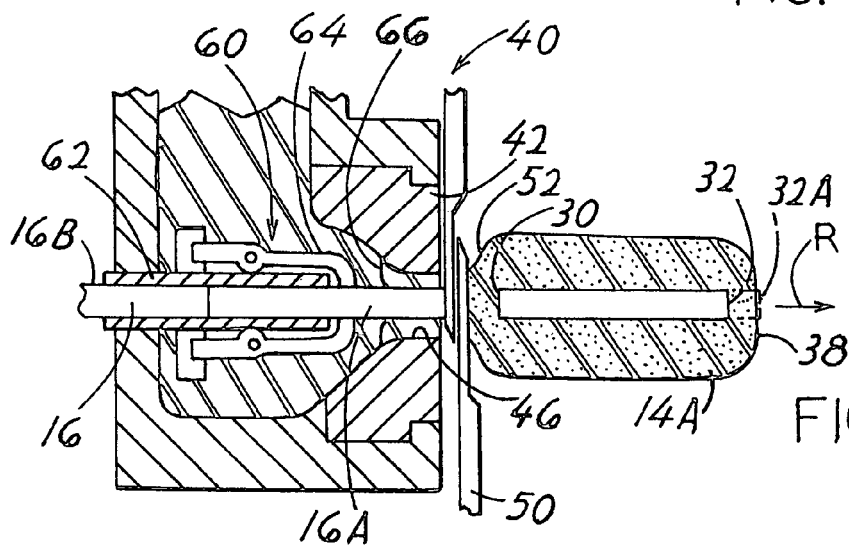
FIG. 3 is a partial sectional view of extrusion apparatus that can be used to mass produce earplugs of the type shown in FIG. 2.

FIG. 3 illustrates apparatus 40 for producing earplugs of the type illustrated at 12 in FIGS. 1 and 2. The apparatus includes an extrusion head 42 that extrudes largely liquid foamable material 44 though a die opening 46 to form an extrusion 52. At the same time, cores 16 are fed into the opening 46 to lie within the earplug bodies 14A as they are extruded. FIG. 3 shows blades 50 which are used to sever the extrusion 52. The apparatus includes a feeder 60 that feeds cores that each have a length L of about two-thirds inch (17 millimeters), into the extrusion head opening 46 to lie in the earplug bodies 14A as they are extruded. The blades 50 are operated to sever the extrusion 52 whenever a predetermined length of extrusion such as one inch, projects out of the extrusion head.

The feeder 60 feeds cores into the extrusion 52 at intervals synchronized with operation of the blades 50. The synchronization assures that the opposite ends 30,32 of each core lies within the body 14A, or at least that the core front end 30 lies recessed from the front end of the earplug body. In FIG. 3, applicant shows a tube 62 containing cores cut from a core device 16B to the proper length and being pushed in the rearward extrusion direction R along the tube. Grippers 64 hold each core such as core 16A for a short period of time and release it to lie in the proper position within the earplug body 14A as the body is extruded. FIG. 3 also shows a few fins 66 that help guide each core to position it at the axis or middle of the extrusion opening 46 while allowing the foamable material 44 to extrude easily into the opening. It is also possible to use a device that grips and pushes each core forwardly and releases it, or to use a continuous core device and to repeatedly cut it a short distance before the extrusion opening. The position of the leading end of each core can be detected within the soft foam extrusion, as by ultrasonic or x-rays, or by applying magnetic or metal material to an end of each core for detection. This facilitates cutting of the continuous extrusion to leave earplugs with core front ends consistently spaced from the body front ends by a distance of a few to several millimeters.

Figure 4:
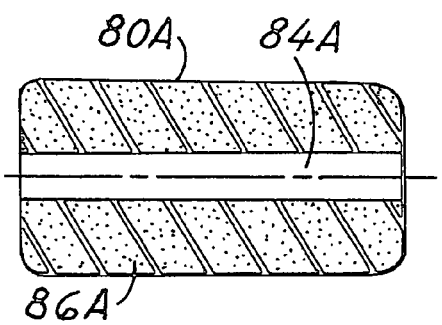
FIG. 4 is a sectional view of an earplug of another embodiment of the invention, shown prior to complete expansion of the earplug body.
Figure 5:
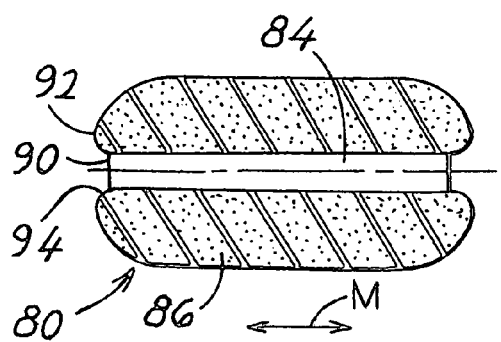
FIG. 5 is a sectional view of the earplug of FIG. 4, shown after expansion of the body.

FIGS. 4 and 5 illustrate an earplug at different stages of its manufacture. At 80A in FIG. 4, the earplug is shown when it is initially molded, as when it emerges from an extrusion head opening and is severed at the head. The earplug ends are slightly rounded as a result of the extruded foam material starting to expand. FIG. 5 shows the earplug at 80 after its foam material has fully foamed and the earplug has cooled to room temperature. The core at 84A in FIG. 4 is shown as it lies within the body 86A immediately after extrusion and cutting. The material of the body 86A has not fully foamed. The body at 86 (FIG. 5) in the finished earplug 80 has expanded to a larger length than the core, resulting in the ends of the core becoming recessed in the body. As mentioned above, this avoids the possibility that the core front end will rub against the ear of the wearer during earplug insertion.

The earplug illustrated in FIG. 5 can be produced in the manner shown in U.S. Pat. Nos. 5,573,015 and 6,659,103 where a continuous core device is fed through an extrusion die opening around a foamable material, to form an extrusion from which earplugs are cut off, as by the blades 50 of FIG. 3. The extrusion is cut very close to the extrusion die whenever a given length (e.g. one inch) of extrusion lies forward of the extrusion head opening. In the present invention, the body expands in length (and usually also in diameter) after being cut to result in a core with a front end that is recessed from the front end 92 of the earplug body. In FIG. 5, the core front end 90 is exposed, because it lies at the end of a passage 94 in the body.

Figure 6:
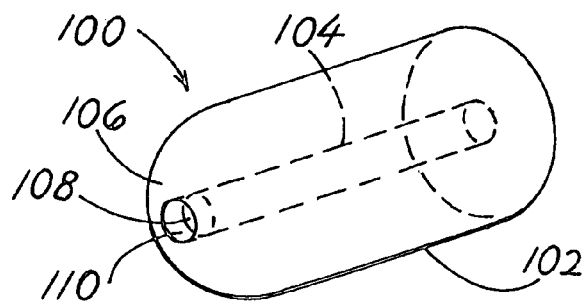
FIG. 6 is an isometric view of an earplug of another embodiment of the invention, wherein a front portion of the core has been removed after molding.
Figure 7:
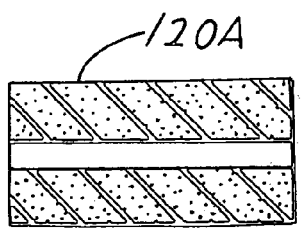
FIG. 7 is a sectional view of an earplug shown prior to its complete manufacture, which has been cut from a solidified extrusion.
Figure 8:
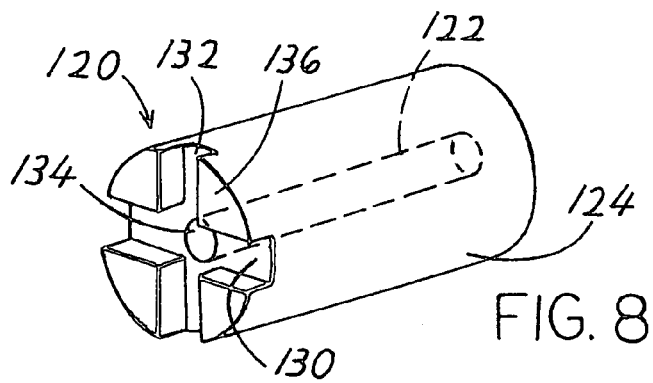
FIG. 8 is an isometric view of the earplug of FIG. 7 after is has been finished by at least one cut across its front end to remove a front portion of the core.

FIG. 6 illustrates an earplug 100 which is altered after being produced by one of the methods described in U.S. Pat. No. 5,573,015. The earplug is initially produced with a body of soft elastomeric material, preferably a foam, and with a core that is stiffer in compression along its front-to-rear length than the body. The core front end initially lies adjacent and almost flush with the front end of the body. The front end of the body is preferably rounded as in FIG. 5, although it can be flat as in FIG. 7. Applicant recesses the core front end by applying a tool to the core front end to remove some of the core initial front end. The core front end can be removed as by a rotary cutter that cuts away core material (and a little body material), or a hot poker that melts core material, to leave the core front end 108 recessed. FIG. 6 shows substantially only the core front portion cut away, to leave a core front end that is recessed from the body front end. FIG. 8 shows a pair of cross-cuts 130,132 formed across the front of an earplug 120 to leave a core front end that is recessed from the body front end.

Instead of forming each earplug by extrusion, it is possible to form each earplug by static molding wherein foamable material is injected or placed in a mold that contains a core with its front end recessed from the body that is to be molded around the core.

Applicant prefers that the rear end of each core lie about flush with or slightly recessed from the rear end of the body. If the core projects rearward of the body rear end, applicant prefers that the core not project more than about three millimeters rearward of the body rear end, so the projecting core does not interfere with pushing of the earplug into the ear canal. With the core rear end lying flush with or slightly recessed from the body rear end, a person can insert the earplug by pressing forwardly against the rear end of the earplug with the index finger or thumb, instead of requiring the person to grasp a rearwardly projecting core end and push it forward with possible flexing of such protruding core part. FIG. 3 shows, in phantom lines, the core positioned so the rear end at 32A lies about flush with the body rear end 38.

Figure 9:
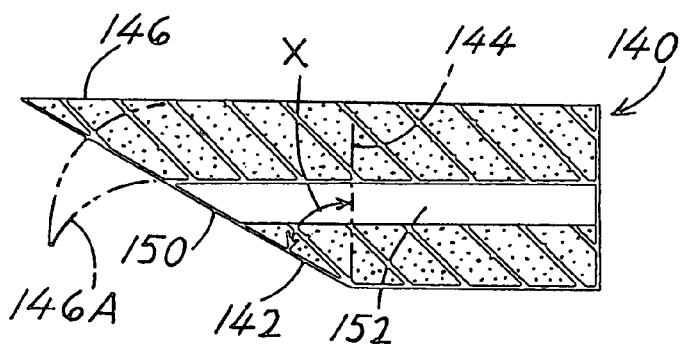
FIG. 9 is a sectional view of an earplug of another embodiment of the invention, wherein the front end of an extrusion has been cut at an angle to its axis.

FIG. 9 illustrates an earplug 140 with a front end cut at an angle X of at least 30° to a plane that is perpendicular to the earplug axis. This results in a flap 146 that can be bent over at 146A to largely cover the front end 150 of the core 152.

Thus, the invention provides a low cost earplug and production method, wherein a longitudinally elongated stiffener, or core lies in a soft elastomeric, preferably foam, body of the earplug, without danger that the front end of the stiff core will rub against the wearer's ear canal during initial insertion of the earplug into the ear canal. The core front end is recessed to lie rearward and preferably a plurality of millimeters rearward, but not more than about 1 centimeter, of the front end of the earplug body. In one earplug, the core front end is covered by body material, while in another earplug the core front end is exposed at the end of a passage. The earplugs with recessed core front ends can be manufactured at low cost by extrusion, by feeding precut cores into an extrusion head while foamable body material is extruded around the core. The core also can be recessed after an extrusion containing a continuous core device has been extruded and cut into lengths of about one inch each, by relying on an expanding body or by cutting away the front portion of the core.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. An earplug comprising:

an earplug body of elastomeric material with a body front portion of a size to enter a human ear canal and block sound, said body front portion having a body front end, said body having a body rear portion with a body rear end;

a core that is elongated in a front-to-rear direction, that lies in said body, and that is stiffer than said body, said core having front and rear ends;

said core is bonded to said body, said core rear end lies forward of said body rear end and said core front end lies rearward of said body front end, and material of said body lies directly behind said core rear end.

2. The earplug described in claim 1 wherein:

said core is encased in said body.

3. An earplug comprising:

an earplug body of elastomeric material with body front portion of a size to enter a human ear canal and block sound, said body front portion having a body front end;

a core that is elongated in a front-to-rear direction, that lies in said body, and that is stiffer than said body, said core being bonded to said body, and said core has a front end that lies rearward of said body front end, said core front end lies a distance A rearward of said body front end, and the distance (B) between a rear end of said body and a rear end of said core is less than said distance A.

4. The earplug described in claim 3 wherein:

said core is encased in said body.

5. The earplug described in claim 3 wherein:

material of said body lies behind the rear end of said core.

6. An earplug comprising:

an earplug body with a body front portion of a size to enter a human ear canal and block sound, said body front portion having a body front end, and said body having a body rear end;

a core that is elongated in a front-to-rear direction, that lies in said body, and that is stiffer than said body;

said core is bonded to said body so said core cannot slide in said body, said core has a front end that lies rearward of said body front end, and said core has a rear end that lies forward of said body front end.

7. The earplug described in claim 6 wherein:

said core is encased in said body.

8. The earplug described in claim 6 wherein:

material of said body lies behind the rear end of said core.

* * * * *